(12) United States Patent
Tsao

(10) Patent No.: US 9,119,947 B2
(45) Date of Patent: Sep. 1, 2015

(54) CLUSTER-TYPE FLUID-CONDUCTING PIPE CONNECTING DEVICE

(75) Inventor: Chih Pam Tsao, New Taipei (TW)

(73) Assignee: CAREMED SUPPLY INC., New Taipei (TW)

( * ) Notice: Subject to any disclaimer, the term of this patent is extended or adjusted under 35 U.S.C. 154(b) by 932 days.

(21) Appl. No.: 13/323,245

(22) Filed: Dec. 12, 2011

(65) Prior Publication Data

US 2013/0147185 A1   Jun. 13, 2013

(51) Int. Cl.
*F16L 17/00* (2006.01)
*A61M 39/10* (2006.01)
*F16L 37/56* (2006.01)

(52) U.S. Cl.
CPC ......... *A61M 39/1011* (2013.01); *A61M 39/105* (2013.01); *F16L 37/56* (2013.01)

(58) Field of Classification Search
USPC .............. 285/377, 120.1, 402, 362, 401, 360, 285/376, 308, 82, 81
See application file for complete search history.

(56) References Cited

U.S. PATENT DOCUMENTS

| | | | | |
|---|---|---|---|---|
| 551,733 A * | 12/1895 | Mullenhoff | ...................... | 285/90 |
| 2,076,918 A * | 4/1937 | Robison | .......................... | 285/82 |
| 2,315,981 A * | 4/1943 | Olson | ........................... | 396/544 |
| 2,648,553 A * | 8/1953 | Ulrich | ........................... | 285/304 |
| 3,470,524 A * | 9/1969 | Culver | ........................... | 439/317 |
| 5,397,196 A * | 3/1995 | Boiret et al. | .................. | 403/348 |
| 5,741,084 A * | 4/1998 | Del Rio et al. | ................ | 403/349 |
| 7,922,214 B2 * | 4/2011 | Nakamura et al. | ............ | 285/316 |
| 9,027,969 B2 * | 5/2015 | Lin | ................................ | 285/402 |

* cited by examiner

*Primary Examiner* — Aaron Dunwoody
(74) *Attorney, Agent, or Firm* — Shimokaji & Associates, P.C.

(57) ABSTRACT

A cluster-type fluid-conducting pipe connecting device includes a base section; a retaining ring fitted to a front of the base section and turnable from a closed position to an open position; the retaining ring and the base section being correspondingly provided at a front end with fixing slots and connection slots, respectively, and a sideward locating slot being formed at a rear end of each fixing slot; a reset structure enabling the retaining ring to automatically return from the open position to the closed position; and a connector having a forward pipe engaging section for fluid-conducting pipes to connect thereto, and a rearward plug section for inserting into the base section and externally provided with stubs that slide into the connection and fixing slots while the retaining ring is in the open position and are locked in the locating slots while the retaining ring is in the closed position.

7 Claims, 6 Drawing Sheets

CLUSTER-TYPE FLUID-CONDUCTING PIPE CONNECTING DEVICE

FIELD OF THE INVENTION

The present invention relates to a fluid-conducting pipe connecting device, and more particularly to a cluster-type fluid-conducting pipe connecting device for conveniently connecting a large number of fluid-conducting pipes to a medical bed at one time.

BACKGROUND OF THE INVENTION

Many patients are bedridden due to illness or injure. Since a bedridden patient can not move freely on bed, he or she tends to gradually lose his or her muscular functions. Moreover, being unable to freely turn on bed, bedsores tend to form on some specific areas of the bedridden patient's body that are frequently subjected to pressure while the patient is lying in bed. In response to these problems, various specially designed medical beds have been developed and introduced into the market to help patients to conveniently change their positions on bed or to distribute their body weight over a larger area.

According to different purposes of use, the medical beds can be actuated through mechanical, power, pneumatic, or hydraulic transmission. Medical beds with different actuation manners have their own advantages and disadvantages. Among others, the medical beds adopting pneumatic/hydraulic transmission are characterized by their safe and stable operation and are therefore widely accepted by users. However, the number of pneumatic/hydraulic pipelines and the difficulty in arranging and laying these pipelines will largely increase when the medical beds have quite complicated design and structure.

Generally, a medical bed, due to its special purpose in use, must allow independent adjustment, such as in inclination, of different bed parts corresponding to the patient's different areas, such as head, trunk, and limbs, so as to provide the patient lying thereon with most suitable supporting force. To achieve such purpose, the medical beds usually require more pipelines and higher pipe arrangement density than other instruments. Further, while all the pipelines must be firmly and stably connected to the medical bed, they must also be arranged as simple as possible to avoid interfering with the movements of nursing personnel. However, the currently available fluid-conducting pipe connection apparently fails to effectively achieve the above requirements. Therefore, it is necessary to develop an improved fluid-conducting pipe connecting device to enable high pipe arrangement density and convenient connection of a large number of pipes to the medical bed at one time.

SUMMARY OF THE INVENTION

A primary object of the present invention is to provide a cluster-type fluid-conducting pipe connecting device that enables convenient and firm connection of a large number of fluid-conducting pipes to, for example, a medical bed at one time, so as to simplify the arrangement and laying of the fluid-conducting pipes.

To achieve the above and other objects, the cluster-type fluid-conducting pipe connecting device according to the present invention includes a base section, a retaining ring, a reset structure, and a connector. The base section includes a flat base plate and a tubular wall axially forward extended from a front side of the base plate; the tubular wall is provided at a front end with a plurality of circumferentially spaced and axially rearward extended connection slots, and on an outer surface with a rotation-limiting structure. And, a plurality of pipe joints are arranged on an area of the base plate enclosed in the tubular wall. The retaining ring is fitted on the tubular wall of the base section, and includes at least one rotation limiter corresponding to the rotation-limiting structure provided on the tubular wall, such that the retaining ring fitted on the tubular wall can only be rotated within a limited angular range relative to the tubular wall between a closed position and an open position. The retaining ring is provided on a front end of its wall with a plurality of spaced fixing slots aligned with the connection slots on the tubular wall; and a locating slot is extended from a rear end of each of the fixing slots. The reset structure is connected to the retaining ring for the retaining ring released from an externally applied force to automatically return to the closed position. The connector has an end configured as a rearward extended plug section for inserting into the tubular wall of the base section, and an axially opposite end configured as a forward extended pipe engaging section for a plurality of fluid-conducting pipes to connect thereto; and the plug section is provided on an outer surface with a plurality of stubs corresponding to the connection slots and slidable in the fixing slots and the connection slots.

In a preferred embodiment, the rotation-limiting structure includes at least one set of spaced first and second stops located along a rear end of the tubular wall of the base section, and the rotation limiter includes a limiting leg rearwardly extended from a rear end of the retaining ring to locate between one set of the first and second stops, such that the retaining ring is rotatable relative to the tubular wall only within an angular range defined between the first and the second stop.

In another preferred embodiment, the reset structure includes at least one elastic arm and a mating stopper. The elastic arm is rearwardly extended from the rear end of the retaining ring, and the stopper is arranged on the rear end of the tubular wall of the base section. When the retaining ring is fitted on the tubular wall of the base section, the elastic arm is firmly abutted against the mating stopper, so that the retaining ring released from an externally applied force is pushed by an elastic force of the elastic arm back to the closed position.

In a further preferred embodiment, the tubular wall of the base section is configured as a cylindrical wall, and the cylindrical wall is provided on an inner surface with at least one alignment structure for the connector to insert into the cylindrical wall at a correct angular position relative to the cylindrical wall; the retaining ring is configured as a cylindrical member for fitly mounting on an outer surface of the cylindrical wall of the base section; and the rearwardly extended plug section of the connector has a configuration corresponding to that of the inner surface of the cylindrical wall and is provided with at least one mating alignment structure corresponding to the alignment structure on the cylindrical wall to ensure that the connector is inserted into the cylindrical wall of the base section at a correct angular position relative to the cylindrical wall.

In a preferred embodiment, the cluster-type fluid-conducting pipe connecting device according to the present invention further includes a ring-shaped cover externally fitted around the retaining ring and at least one holding-down plate mounted to the front side of the base plate of the base section. The ring-shaped cover is provided at a front top with an opening for the connector to extend therethrough, along the opening with a plurality of spaced notches for the stubs on the plug section of the connector to pass therethrough, and at a rear end with a locating flange. And, the holding-down plate is configured corresponding to the base section and allows the ring-shaped cover to extend therethrough. Further, the holding-down plate is provided at positions in contact with the ring-shaped cover with an engaging recess for engaging with the locating flange of the ring-shaped cover.

In another preferred embodiment, the ring-shaped cover is provided on an inner surface with a plurality of sliding slots, and the retaining ring is correspondingly provided on an outer surface with a plurality of protrusions for engaging with the sliding slots, so that the ring-shaped cover externally fitted around the retaining ring is able to bring the retaining ring to rotate synchronously.

In a further preferred embodiment, the connection slots are configured as straight slots having identical slot width, the fixing slots are configured as wedge-shaped slots respectively having a flared front opening and a narrowed rear end, and the locating slots are sidewardly extended from the rear ends of the fixing slots, such that each of the fixing slots and the locating slot sidewardly extended from the rear end thereof together form an L-shaped slot.

The cluster-type fluid-conducting pipe connecting device according to the present invention is characterized by having a base section; a retaining ring fitted around a front tubular wall of the base section; a reset structure; and a connector. The retaining ring and the tubular wall are correspondingly provided at a front end with fixing slots and connection slots, respectively. And, a locating slot is sidewardly extended from a rear end of each fixing slot, so that the locating slot and the fixing slot together form a substantially L-shaped slot. The retaining ring can be turned relative to the base section from a closed position to an open position. The reset structure is connected to the retaining ring for the retaining ring released from an externally applied force to automatically return to the closed position. The connector has a rearward extended plug section for inserting into the tubular wall of the base section, and a forward extended pipe engaging section for a plurality of fluid-conducting pipes to connect thereto. The plug section is provided on an outer surface with a plurality of stubs corresponding to the connection slots. The stubs slide into the connection slots and the fixing slots when the connector is inserted into the tubular wall of the base section and force the retaining ring to rotate to the open position. And, when the stubs move into the locating slots, the reset structure elastically resets the retaining ring to the closed position and thereby locks the stubs in the locating slots, allowing the connector to firmly connect to the base section.

With the above arrangements, the present invention allows a user to connect multiple fluid-conducting pipes to an apparatus, such as a medical bed, at one time to largely simplify the arrangement of fluid-conducting pipes.

BRIEF DESCRIPTION OF THE DRAWINGS

The structure and the technical means adopted by the present invention to achieve the above and other objects can be best understood by referring to the following detailed description of the preferred embodiments and the accompanying drawings, wherein.

DETAILED DESCRIPTION OF THE PREFERRED EMBODIMENTS

Figure 1:
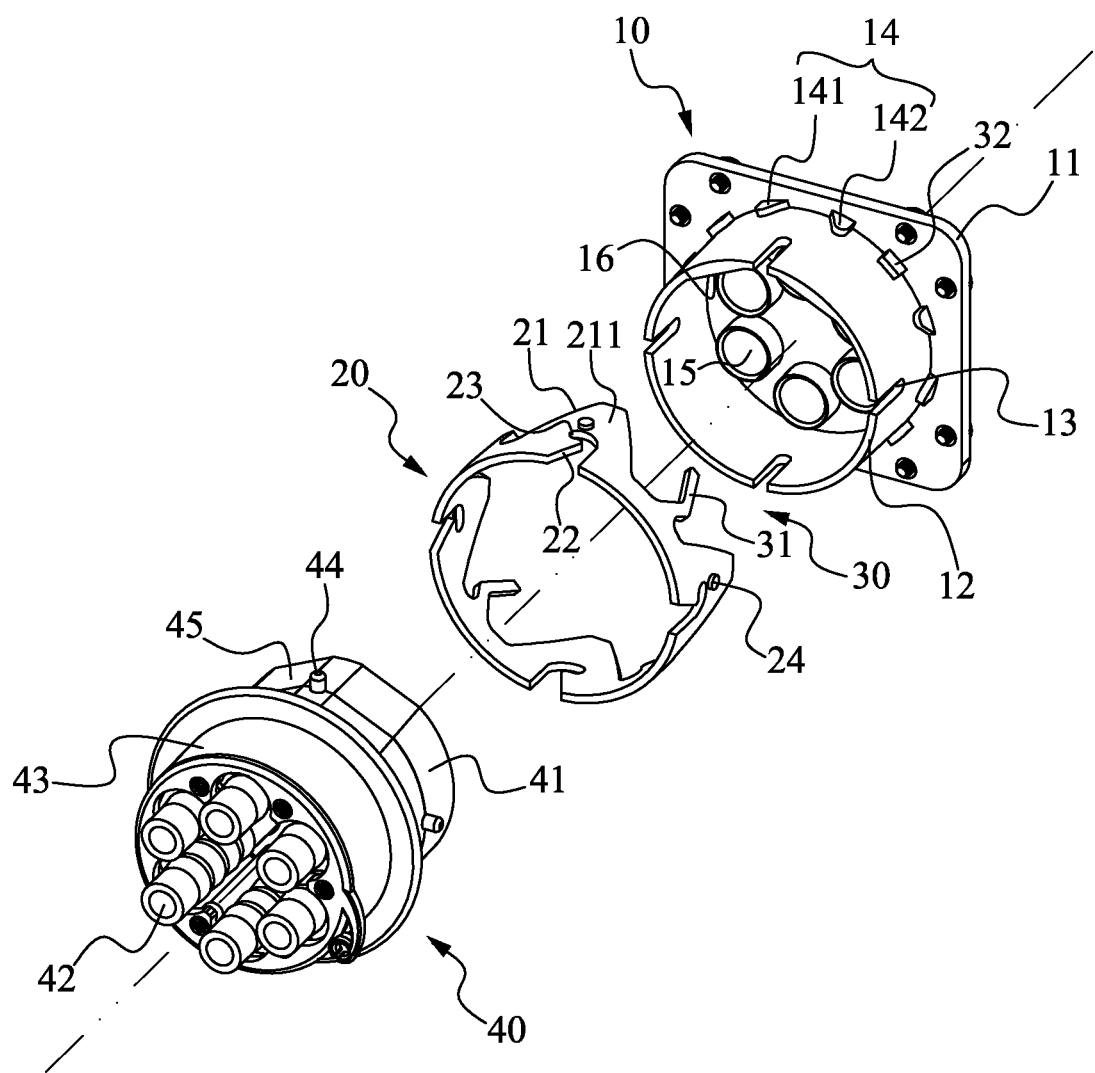
FIG. 1 is an exploded perspective view of a cluster-type fluid-conducting pipe connecting device according to a first embodiment of the present invention.

The present invention will now be described with some preferred embodiments thereof and with reference to the accompanying drawings. For the purpose of easy to understand, elements that are the same in the preferred embodiments are denoted by the same reference numerals.

Please refer to FIG. 1 that is an exploded perspective view of a cluster-type fluid-conducting pipe connecting device according to a first embodiment of the present invention. As shown, the cluster-type fluid-conducting pipe connecting device in the first embodiment includes a base section 10, a retaining ring 20, a reset structure 30, and a connector 40.

The base section 10 includes a flat base plate 11 and a tubular wall 12 axially forward extended from a front side of the base plate 11. The tubular wall 12 is provided with a plurality of circumferentially spaced connection slots 13, which axially rearward extend from a front end of the tubular wall 12 by a predetermined distance. The tubular wall 12 is further externally provided along a rear end with a rotation-limiting structure 14. And, a plurality of pipe joints 15 is arranged on an area of the base plate 11 enclosed in the tubular wall 12.

The retaining ring 20 is fitted on an outer side of the tubular wall 12 of the base section 10, and includes at least one rotation limiter 21 corresponding to the rotation-limiting structure 14 provided on the tubular wall 12, such that the retaining ring 20 fitted on the tubular wall 12 can only rotate within a limited angular range relative to the tubular wall 12. In the illustrated first embodiment, the rotation-limiting structure 14 includes multiple sets of stops, and each set of stops includes a first stop 141 and a second stop 142 spaced from each other; and the rotation-limiter 21 is configured as a limiting leg 211 rearwardly extended from the retaining ring 20 to locate between one set of the first and second stops 141, 142, such that the retaining ring 20 is rotatable relative to the tubular wall 12 only within an angular range defined between the first and the second stop 141, 142. The retaining ring 20 is provided on a front end of its wall with a plurality of spaced fixing slots 22. In the illustrated first embodiment, the connection slots 13 on the tubular wall 12 are straight slots having identical slot width, and each of the fixing slots 22 on the retaining ring 20 is configured as a wedge-shaped slot having a flared opening and a narrowed rear end. Further, a locating slot 23 is sidewardly extended from the rear end of the fixing slot 22, so that the fixing slot 22 and the locating slot 23 together form a substantially L-shaped slot, which cooperates with a corresponding one of the connection slots 13 to provide a retaining structure that is closed or opened according to an angular position of the retaining ring 20 relative to the tubular wall 12.

The reset structure 30 is provided on the retaining ring 20 for automatically resetting the retaining ring 20 to a closed position when the retaining ring 20 is released from any external force applied thereto. In the illustrated first embodiment, the reset structure 30 includes at least one elastic arm 31 and a mating stopper 32. The elastic arm 31 is rearwardly extended from a rear end of the retaining ring 20, and the stopper 32 is arranged at the rear end of the tubular wall 12 of the base section 10 with the elastic arm 31 abutting on the mating stopper 32. When the retaining ring 20 is fitted on the base section 10, the elastic arm 31 is firmly abutted against the mating stopper 32 to produce a force for the retaining ring 20 to rotate clockwise, so that the retaining ring 20 is pushed to the closed position.

The connector 40 has an end configured as a rearward extended plug section 41 for inserting into the tubular wall 12 of the base section 10, and an axially opposite end configured as a forward extended pipe engaging section 43 for a plurality of fluid-conducting pipes 42 to connect thereto. The plug section 41 is provided on an outer surface with a plurality of stubs 44 corresponding to the connection slots 13. In the illustrated first embodiment, to ensure exact alignment of the fluid-conducting pipes 42 on the connector 40 with the pipe joints 15 on the base section 10 when the plug section 41 is inserted into the base section 10, at least one alignment structure 16 is provided on an inner surface of the tubular wall 12 and at least one mating alignment structure 45 is correspondingly provided on the outer surface of the plug section 41, so that the connector 40 can be inserted into the tubular wall 12 at a correct angular position relative to the tubular wall 12. In the illustrated first embodiment, the alignment structure 16 is configured as a flat surface formed on a round inner surface of the tubular wall 12 of the base section 10 to extend from the front end to the rear end of the tubular wall 12; and the mating alignment structure 45 is configured as a flat surface formed on the round outer surface of the plug section 41 corresponding to the alignment structure 16. By aligning the mating alignment structure 45 with the alignment structure 16, the connector 40 can be inserted into the tubular wall 12 at a correct angular position.

Figure 2:
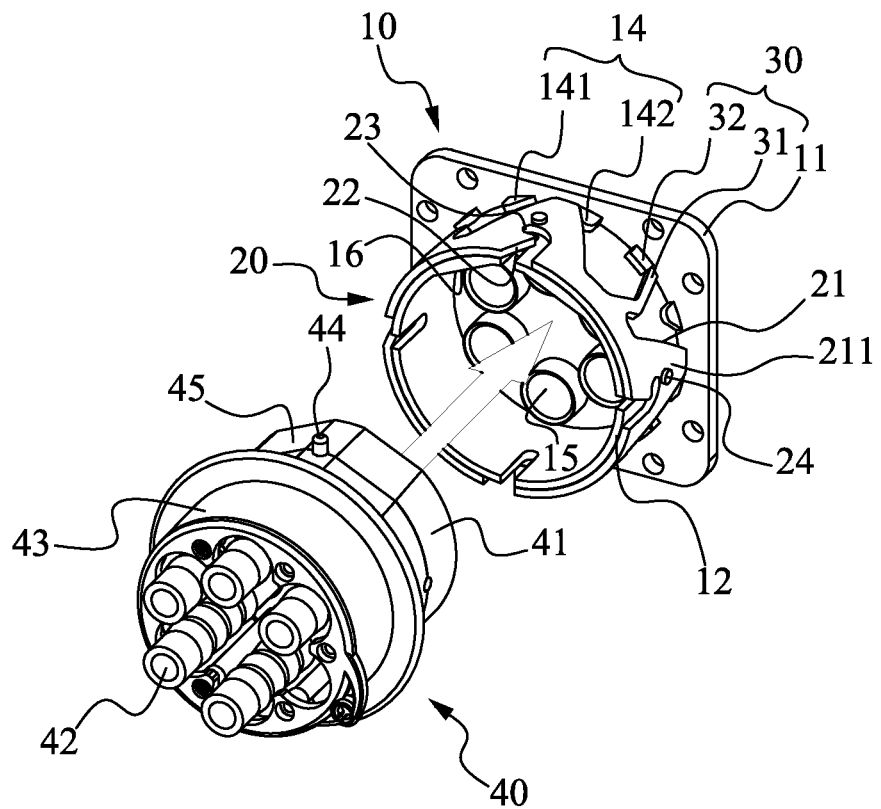
FIG. 2 is a perspective view showing the manner of assembling the cluster-type fluid-conducting pipe connecting device according to the first embodiment of the present invention.
Figure 3:
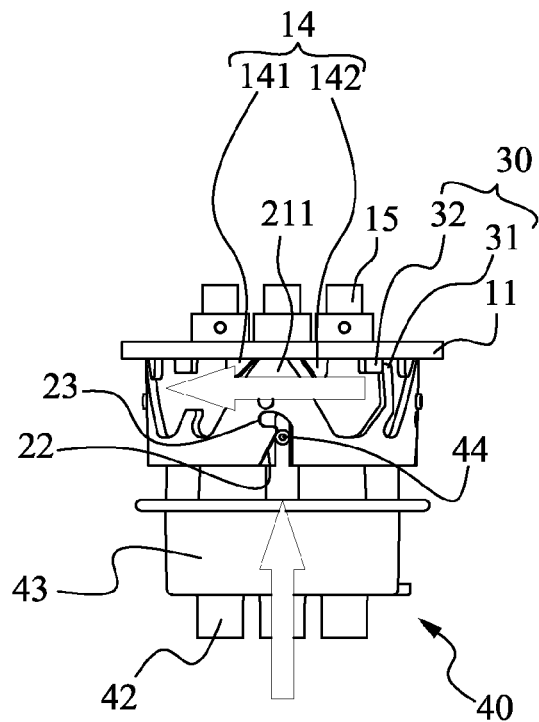
FIG. 3 is a top view showing the manner of assembling the cluster-type fluid-conducting pipe connecting device according to the first embodiment of the present invention.
Figure 3:
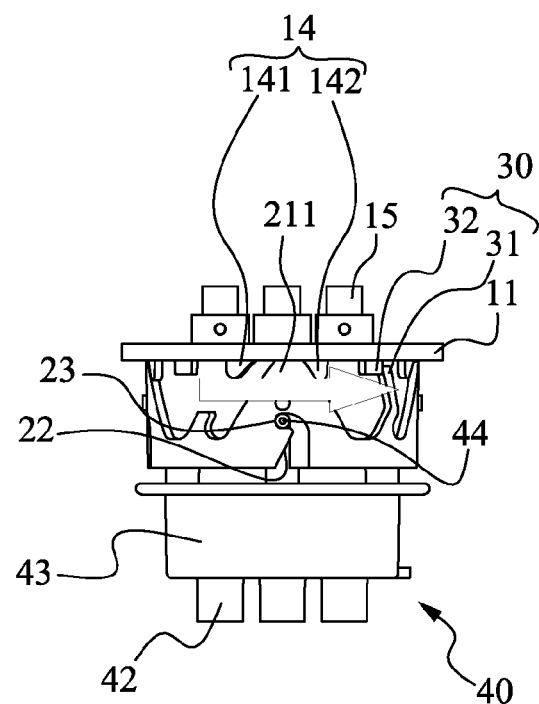

Please refer to FIGS. 2 and 3. To utilize the cluster-type fluid-conducting pipe connecting device of the present invention to connect to a large number of pipes to, for example, a medical bed, a user needs only to plug the connector 40 into the base section 10 from a front end thereof with the mating alignment structure 45 aligned with the alignment structure 16, and the fluid-conducting pipes 42 on the connector 40 can be correctly aligned with and connected to the pipe joints 15 on the base section 10. And, in the process of connection, each of the stubs 44 will push against one lateral side of the corresponding wedge-shaped fixing slot 22 to slide into the latter and the connection slot 13 and thereby forces the retaining ring 20 to rotate counterclockwise from the closed position into the open position. When the stubs 44 have slid to the rear ends of the fixing slots 22, they will further move into the locating slots 23. At this point, the retaining ring 20 automatically rotates reversely to the closed position again under the action of the reset structure 30, and the stubs 44 are locked in the locating slots 23 to complete the connection of the fluid-conducting pipes 42 to the pipe joints 15.

Figure 4:
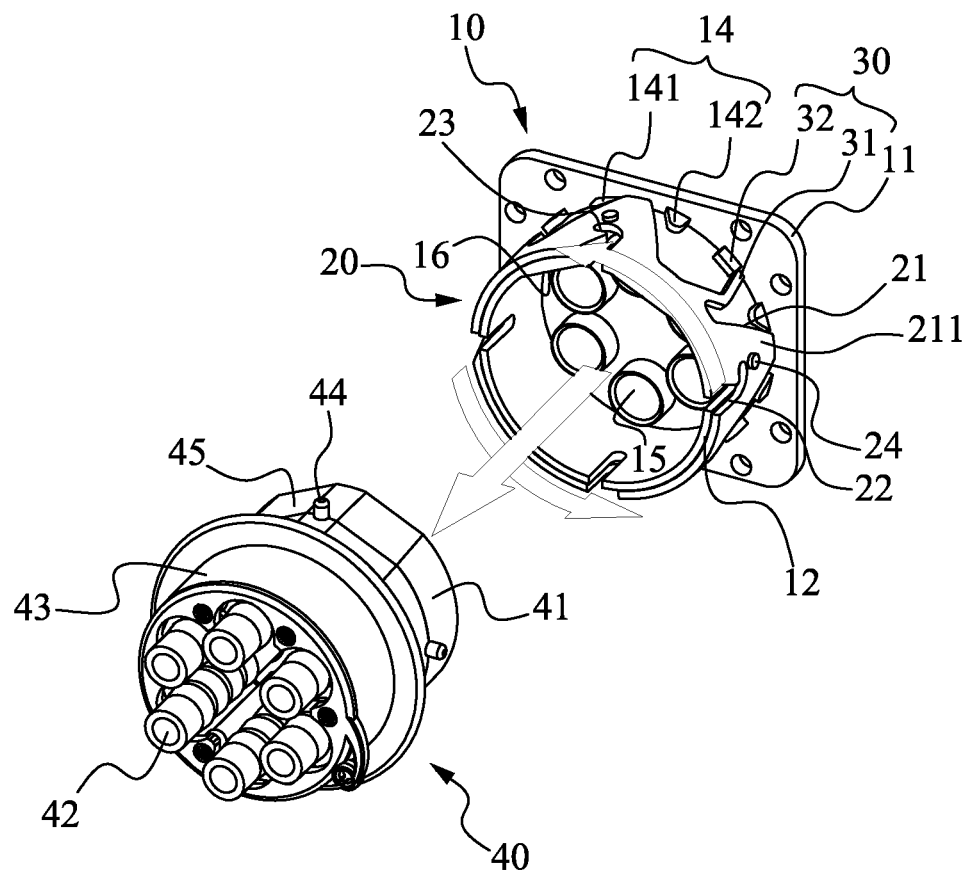
FIG. 4 is a perspective view showing the manner of disassembling the cluster-type fluid-conducting pipe connecting device according to the first embodiment of the present invention.

Please refer to FIG. 4. When it is desired to disconnect the fluid-conducting pipes 42 from the pipe joints 15, the user needs only to turn the retaining ring 20 counterclockwise to its open position and unlocks the stubs 44 from the locating slots 23. Then, the user may pull the connector 40 out of the base section 10.

Figure 5:
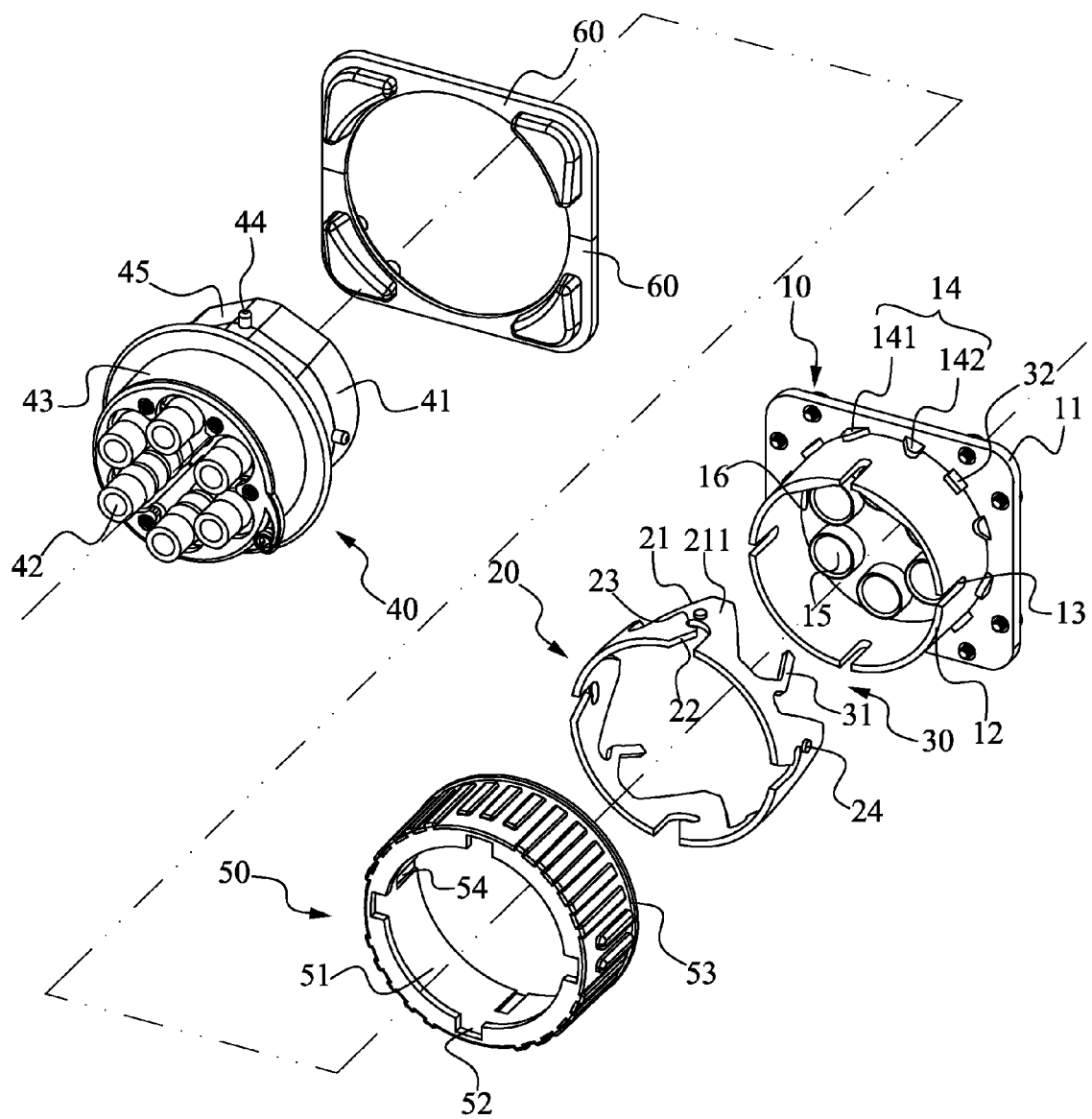
FIG. 5 is an exploded perspective view of a cluster-type fluid-conducting pipe connecting device according to a second embodiment of the present invention.
Figure 6:
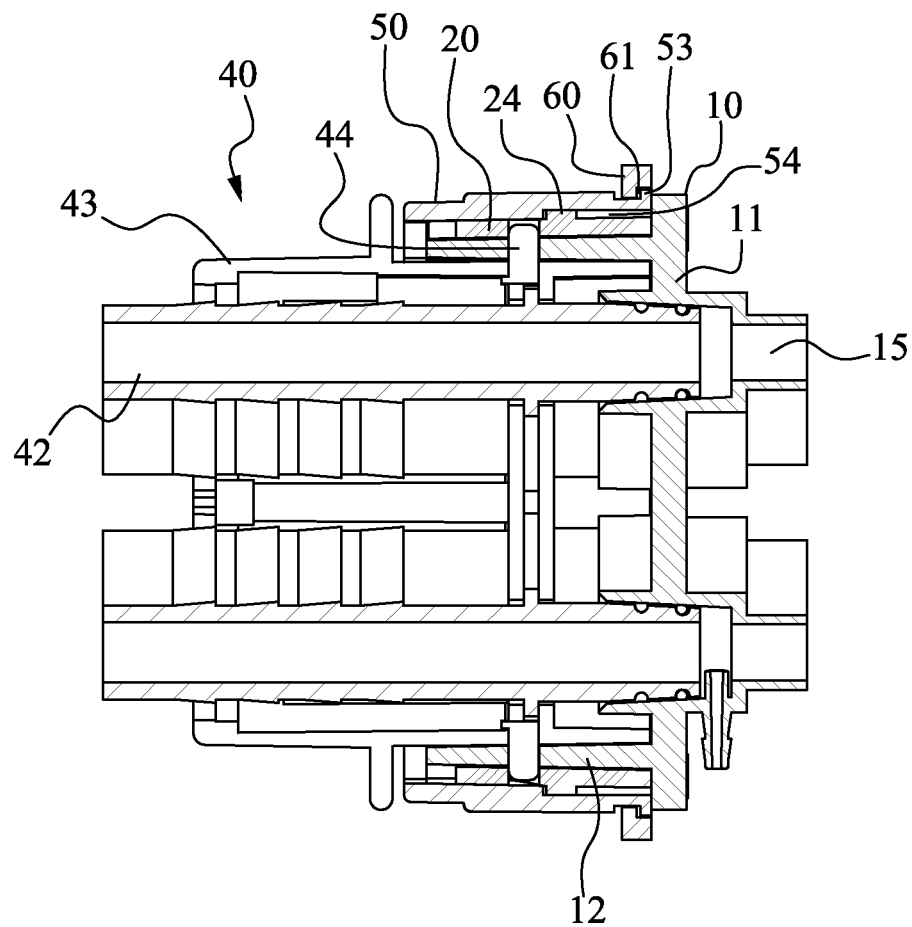
FIG. 6 is an assembled sectional view of the cluster-type fluid-conducting pipe connecting device according to the second embodiment of the present invention.

FIGS. 5 and 6 are exploded perspective view and assembled sectional view, respectively, of a cluster-type fluid-conducting pipe connecting device according to a second embodiment of the present invention. As shown, in the second embodiment, the cluster-type fluid-conducting pipe connecting device further includes a ring-shaped cover 50 and at least one holding-down plate 60. The ring-shaped cover 50 is externally fitted around the retaining ring 20, so that the retaining ring 20 is restricted to the base section 10 by the ring-shaped cover 50 without the risk of separating from the front end of the base section 10. The holding-down plate 60 is configured corresponding to the base section 10 for mounting to the front side of the base plate 11 of the base section 10 while allowing the ring-shaped cover 50 to extend therethrough.

Further, for the connector 40 to function as usual without being hindered by the ring-shaped cover 50, the ring-shaped cover 50 is provided at a front top with an opening 51 for the connector 40 to extend therethrough, and a plurality of notches 52 is spaced along the opening 51 corresponding to the stubs 44, so that the stubs 44 can pass through the ring-shaped cover 50 via the notches 52 when the connector 40 is extended through the opening 51. Further, to hold the ring-shaped cover 50 to the front of the base section 10 with the holding-down plate 60, the ring-shaped cover 50 is provided at a rear end with a locating flange 53, and the holding-down plate 60 is provided at positions in contact with the ring-shaped cover 50 with an engaging recess 61 for engaging with the locating flange 53. Therefore, when the holding-down plate 60 is screwed to the base section 10, the engaging recess 61 is engaged with the locating flange 53, and the ring-shaped cover 50 along with the retaining ring 20 are held to the front side of the base section 10 by the holding-down plate 60.

In the illustrated second embodiment, the ring-shaped cover 50 is provided on an inner surface with a plurality of sliding slots 54, and the retaining ring 20 is correspondingly provided on an outer surface with a plurality of protrusions 24 for engaging with the sliding slots 54. Therefore, the ring-shaped cover 50 externally fitted around the retaining ring 20 can bring the latter to rotate synchronously, and a user may conveniently turn the ring-shaped cover 50 to move the retaining ring 20 to its open position. Further, the ring-shaped cover 50 is provided on an outer surface with a plurality of anti-slip flutes for the user to turn the ring-shaped cover 50 easily.

In summary, the cluster-type fluid-conducting pipe connecting device according to the present invention includes a base section, a retaining ring fitted around a front tubular wall of the base section, a reset structure, and a connector. The retaining ring and the tubular wall are correspondingly provided at a front end with fixing slots and connection slots, respectively. And, a locating slot is sidewardly extended from a rear end of each fixing slot, so that the locating slot and the fixing slot together form a substantially L-shaped slot. The retaining ring can be turned relative to the tubular wall of the base section from a closed position to an open position. The reset structure is connected to the retaining ring for the retaining ring released from an externally applied force to automatically return to the closed position. The connector has a rearward extended plug section for inserting into the tubular wall of the base section, and a forward extended pipe engaging section for a plurality of fluid-conducting pipes to connect thereto. The plug section is provided on an outer surface with a plurality of stubs corresponding to the connection slots. The stubs slide into the connection slots and the fixing slots when the connector is inserted into the tubular wall of the base section and force the retaining ring to rotate to the open position. And, when the stubs move into the locating slots, the reset structure elastically resets the retaining ring to the closed position and thereby locks the stubs in the locating slots, allowing the connector to firmly connect to the base section. With the above arrangements, the present invention allows a user to connect multiple fluid-conducting pipes to a medical bed, for example, at one time to largely simplify the arrangement of fluid-conducting pipes.

The present invention has been described with some preferred embodiments thereof and it is understood that many changes and modifications in the described embodiments can be carried out without departing from the scope and the spirit of the invention that is intended to be limited only by the appended claims.

What is claimed is:

1. A cluster-type fluid-conducting pipe connecting device, comprising:

a base section including a flat base plate and a tubular wall axially forward extended from a front side of the base plate; the tubular wall being provided at a front end with a plurality of circumferentially spaced and axially rearward extended connection slots, and on an outer surface with a rotation-limiting structure; and a plurality of pipe joints being arranged on an area of the base plate enclosed in the tubular wall;

a retaining ring being fitted on the tubular wall of the base section, and including at least one rotation limiter corresponding to the rotation-limiting structure provided on the tubular wall, such that the retaining ring fitted on the tubular wall can only be rotated within a limited angular range relative to the tubular wall between a closed position and an open position; the retaining ring being provided on a front end of its wall with a plurality of spaced fixing slots aligned with the connection slots on the tubular wall; and a locating slot being extended from a rear end of each of the fixing slots;

a reset structure being connected to the retaining ring for the retaining ring released from an externally applied force to automatically return to the closed position thereof; and a connector having an end configured as a rearward extended plug section for inserting into the tubular wall of the base section, and an axially opposite end configured as a forward extended pipe engaging section for a plurality of fluid-conducting pipes to connect thereto; and the plug section being provided on an outer surface with a plurality of stubs corresponding to the connection slots and slidable in the fixing slots and the connection slots.

2. The cluster-type fluid-conducting pipe connecting device as claimed in claim 1, wherein the rotation-limiting structure includes at least one set of spaced first and second stops located along a rear end of the tubular wall of the base section, and the rotation limiter includes a limiting leg rearwardly extended from a rear end of the retaining ring to locate between one set of the first and second stops, such that the retaining ring is rotatable relative to the tubular wall only within an angular range defined between the first and the second stop.

3. The cluster-type fluid-conducting pipe connecting device as claimed in claim 1, wherein the reset structure includes at least one elastic arm and a mating stopper; the elastic arm being rearwardly extended from a rear end of the retaining ring, and the mating stopper being arranged on a rear end of the tubular wall of the base section; whereby when the retaining ring is fitted on the tubular wall of the base section, the elastic arm is firmly abutted against the mating stopper, so that the retaining ring released from an externally applied force is pushed by an elastic force of the elastic arm back to the closed position.

4. The cluster-type fluid-conducting pipe connecting device as claimed in claim 1, wherein the tubular wall of the base section is configured as a cylindrical wall, and the cylindrical wall being provided on an inner surface with at least one alignment structure for the connector to insert into the cylindrical wall at a correct angular position relative to the cylindrical wall; the retaining ring being configured as a cylindrical member for fitly mounting on an outer surface of the cylindrical wall of the base section; and the rearwardly extended plug section of the connector having a configuration corresponding to that of the inner surface of the cylindrical wall and being provided on an outer surface with at least one mating alignment structure corresponding to the alignment structure on the cylindrical wall to ensure that the connector is inserted into the cylindrical wall of the base section at a correct angular position relative to the cylindrical wall.

5. The cluster-type fluid-conducting pipe connecting device as claimed in claim 1, further comprising a ring-shaped cover externally fitted around the retaining ring and at least one holding-down plate mounted to the front side of the base plate of the base section; the ring-shaped cover being provided at a front top with an opening for the connector to extend therethrough, along the opening with a plurality of spaced notches for the stubs on the plug section of the connector to pass therethrough, and at a rear end with a locating flange; and the holding-down plate being configured corresponding to the base section and allowing the ring-shaped cover to extend therethrough, and being provided at positions in contact with the ring-shaped cover with an engaging recess for engaging with the locating flange of the ring-shaped cover.

6. The cluster-type fluid-conducting pipe connecting device as claimed in claim 5, wherein the ring-shaped cover is provided on an inner surface with a plurality of sliding slots, and the retaining ring is correspondingly provided on an outer surface with a plurality of protrusions for engaging with the sliding slots, so that the ring-shaped cover externally fitted around the retaining ring is able to bring the retaining ring to rotate synchronously.

7. The cluster-type fluid-conducting pipe connecting device as claimed in claim 1, wherein the connection slots are configured as straight slots having identical slot width, the fixing slots are configured as wedge-shaped slots respectively having a flared front opening and a narrowed rear end, and the locating slots are sidewardly extended from the rear ends of the fixing slots, such that each of the fixing slots and the locating slot sidewardly extended from the rear end thereof together form an L-shaped slot.

\* \* \* \* \*